United States Patent
Fauerbach et al.

(10) Patent No.: US 11,073,515 B2
(45) Date of Patent: Jul. 27, 2021

(54) METHOD FOR PHOTOBLEACHING STAINED CELLS

(71) Applicant: Miltenyi Biotec GmbH, Bergisch Gladbach (DE)

(72) Inventors: Jonathan Fauerbach, Rösrath (DE); Christian Dose, Kürten, MA (US); Thomas Rockel, Düsseldorf (DE); Veronika Rudolf, Bergisch Gladbach (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 233 days.

(21) Appl. No.: 16/192,805

(22) Filed: Nov. 16, 2018

(65) Prior Publication Data

US 2019/0162721 A1     May 30, 2019

(30) Foreign Application Priority Data

Nov. 27, 2017 (EP) .................... 17203699

(51) Int. Cl.
| | |
|---|---|
| *G01N 33/543* | (2006.01) |
| *G01N 33/542* | (2006.01) |
| *G01N 33/53* | (2006.01) |
| *G01N 33/58* | (2006.01) |

(52) U.S. Cl.
CPC ... *G01N 33/54353* (2013.01); *G01N 33/5306* (2013.01); *G01N 33/542* (2013.01); *G01N 33/582* (2013.01)

(58) Field of Classification Search
CPC ............. G01N 33/5306; G01N 33/542; G01N 33/54353; G01N 33/582
See application file for complete search history.

(56) References Cited

U.S. PATENT DOCUMENTS

| | | | | |
|---|---|---|---|---|
| 6,150,173 | A * | 11/2000 | Schubert | .................. G01N 1/30 |
| | | | | 422/504 |
| 7,741,045 | B2 | 6/2010 | Gerdes et al. | |
| 7,776,562 | B2 | 8/2010 | Busch et al. | |
| 9,670,318 | B2 * | 6/2017 | Dose | ....................... C08G 65/48 |
| 2007/0031371 | A1 * | 2/2007 | McManus | .............. A61K 31/74 |
| | | | | 424/78.37 |
| 2016/0187326 | A1 * | 6/2016 | Dose | .................... G01N 33/537 |
| | | | | 435/7.24 |

* cited by examiner

*Primary Examiner* — Galina M. Yakovleva
(74) *Attorney, Agent, or Firm* — Jaquelin K. Spong

(57) ABSTRACT

The invention is directed to a method for detecting a target moiety in a sample of biological specimens by:
 a) providing at least one conjugate with the general formula (I) $X_n$—P—$Y_m$,
 b) contacting the sample of biological specimens with at least one conjugate, thereby labeling the target moiety recognized by the antigen recognizing moiety Y with the conjugate
 c) exciting the labelled target moieties with light having a wavelength within the absorbance spectrum of fluorescent moiety X
 d) detecting the labelled target moieties by detecting the fluorescence radiation and
 e) degrading the fluorescent moiety X of the labelled target moieties by irradiating the conjugate with light having a wavelength within the absorbance spectrum of fluorescent moiety X Use of the method in fluorescence microscopy, flow cytometer, spectrofluorometry, cell separation, pathology or histology.

6 Claims, 3 Drawing Sheets

METHOD FOR PHOTOBLEACHING STAINED CELLS

CROSS REFERENCE TO RELATED APPLICATIONS

This US non-Provisional patent application claims priority to EP17203699.8 filed in European Patent Convention on Nov. 27, 2017. This application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

The present invention is directed to a process for detection or identification of target moieties or target cells from a cell sample.

Fluorescent dyes conjugated to one or more antibodies are commonly used for immunofluorescence analysis. A vast number of variants in view of antibodies, fluorescent dyes, flow cytometers, flow sorters, and fluorescence microscopes has been developed in the last two decades to enable specific detection and isolation of target cells.

It is known to utilize fluorescent dyes for isolation or detection of target cells which can be removed or destroyed after detection. For example U.S. Pat. No. 7,776,562 discloses a method of reversible fluorescent labeling based on indirect, non-covalent labeling of target cells with reversible peptide/MHC-Multimers or Fab-Streptamers.

In order to reduce the fluorescence radiation after detection, GB2372256 discloses a process to quench fluorescence radiation by providing a conjugate comprising a plurality of fluorescent dyes attached via a linker to an antibody. The high density of fluorescent dyes will quench the fluorescence signals. Furthermore, GB2372256 describes to enzymatic degrade the linker in order to release fluorescent dyes from the conjugate. The released fluorescent dyes are not subject to self-quenching, resulting in more intense fluorescence signals, i.e. in better resolution.

Elimination of the fluorescence signal is essential for immunofluorescence technologies based on sequentially staining specimen. These technologies have been shown to provide a higher multiplexing potential compared to standard procedures using simultaneously labeling and detection. However, these technologies are based on oxidative destruction of conjugated fluorescent moieties by chemical bleaching procedures (U.S. Pat. No. 7,741,045 B2, EP 0810 428 B1 or DE10143757) or in the case of photobleaching based methods, the rate of bleaching is slower to the methods presented here.

The main intention of the prior art was to provide dyes or conjugates comprising such dyes which to emit fluorescence radiation as intense as possible i.e. with a maximum quantum yield. In order to provide reliable and reproducible signals, the dyes are designed to be as stable as possible. While these properties are advantageous for cell detection and cell separation like a FACS process, they prevent the cells from being repeatedly stained and detected.

SUMMARY

It was therefore an object of the invention to provide an enhanced method for specific labelling and detection of a target in or on a sample of a biological specimen and subsequent degrading the detection moiety in order to enable further labelling and detection cycles.

Surprisingly it was found that conjugates composed of an antigen binding moiety linked via a spacer to a detection moiety having both a higher quantum yield (and thus higher brightness) and a reduced light stability which can be easily degraded by light if the spacer is a branched PEG oligomer or polymer, provided with a plurality of oligomer PEG sidechains, i.e. with a certain degree of branching, and the detection moieties are covalently linked to the branched PEG. Without being bound to this theory, it is believed that the branched PEG oligomer or polymer "wraps" the detection moieties which are covalently attached to it, resulting in a closer contact and a higher quantum yield for light-induced oxidative destruction of the detection moieties.

Object of the invention is therefore a method for detecting a target moiety in a sample of biological specimens by:

a) providing at least one conjugate with the general formula (I) $X_n$—P—$Y_m$, with X is a fluorescent moiety, Y an antigen recognizing moiety, n, m are integers between 1 and 100 and P is a spacer comprising polyethyleneglycol according to general formula I

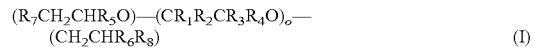

$$(R_7CH_2CHR_5O)—(CR_1R_2CR_3R_4O)_o—(CH_2CHR_6R_8) \quad (I)$$

Wherein R1 to R8 are independently H or a branched or a linear oligomer of ethylene glycol with at least 1 and a maximum of 20000 repeating units or a covalent bond to Y or X, with the provisio that at least two of R1 to R8 are covalent bonds to Y or X and o is an integer of 1-500 b) contacting the sample of biological specimens with at least one conjugate, thereby labeling the target moiety recognized by the antigen recognizing moiety Y with the conjugate c) exiting the labelled target moieties with light having a wavelength within the absorbance spectrum of fluorescent moiety X d) detecting the labelled target moieties by detecting the fluorescence radiation emitted by the fluorescent moiety and e) degrading the fluorescent moiety X of the labelled target moieties by irradiating the conjugate with light having a wavelength within the absorbance spectrum of fluorescent moiety X for a time sufficient to deliver enough energy to reduce the fluorescence radiation emitted by the fluorescent moiety at least by 75% of the initial fluorescence radiation.

Irradiation of the conjugate may be performed by a white wide spectrum light source, a mono wavelength laser or an LED having a wavelength within the absorbance spectrum of fluorescent moiety.

Due to the spacer P, degradation of the fluorescent moiety X is significantly faster than without it, which results in an accelerated and complete quenching of the emission signal. This enables repetitive staining and de-staining process where same or different conjugates provided with same or different fluorescent moieties X and/or antigen recognizing moieties Y may be subsequently applied to the same cells in order to stain different targets or the same target with same or different dyes.

These and other features and advantages are described in, or are apparent from, the following detailed description.

BRIEF DESCRIPTION OF THE DRAWINGS

Various exemplary details are described with reference to the accompanying drawings, which however, should not be taken to limit the invention to the specific embodiments shown but are for explanation and understanding only.

DETAILED DESCRIPTION

Figure 1:
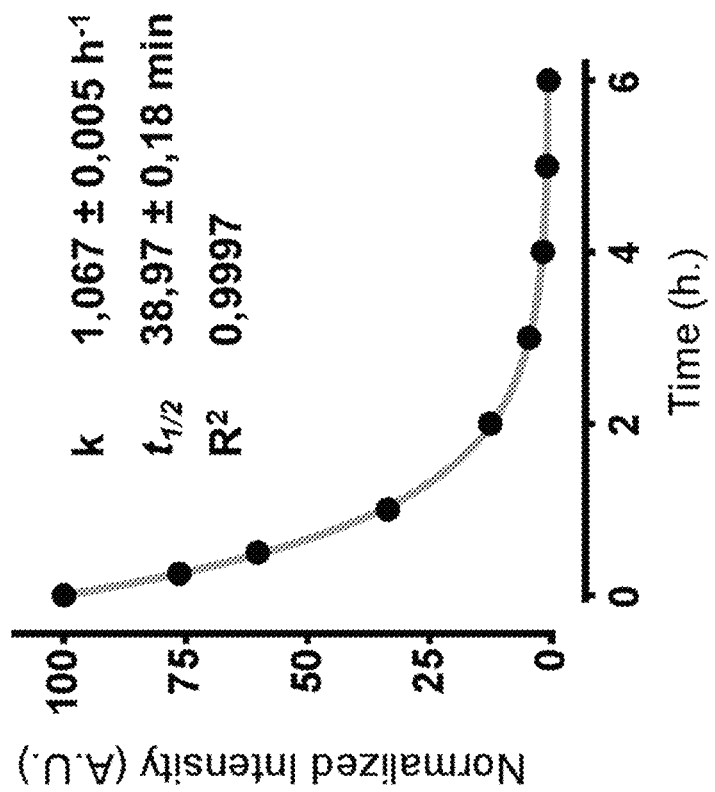
FIG. 1 shows schematic disintegration of a xanthene dye by light with a mono-exponential decay fit $f(x)=y_0*e^{-k*\gamma}$, $\tau=1/k$ and $t_{1/2}=\tau*\ln(2)$

In the method of the invention, the conjugate is irradiated with light having a wavelength within the absorbance spectrum of fluorescent moiety X in order to reduce the fluorescence radiation emitted by the fluorescent moiety so much that any residual fluorescence radiation from a first staining cycle does not interfere with subsequent staining and detection cycles. In general, reduction by at least by 75% of the initial fluorescence radiation is deemed sufficient, but in order to achieve a higher quality of detection i.e. to reduce background radiation not originating from the staining step of interest, it is preferred to reduce fluorescence radiation by at least by 85%, more preferred at least by 95% and most preferred by at least 99%. While a reduction of 100% would be best, there is a trade-off with quenching quality and overall process duration.

In an alternative definition, degrading the fluorescent moiety X of the labelled target moieties is performed by irradiating the conjugate with light having a wavelength within the absorbance spectrum of fluorescent moiety X for a time sufficient to deliver enough energy to reduce the half-life of the fluorescence radiation emitted by the fluorescent moiety. The degradation rate given by the value of k from the mono-exponential decay fit analysis of the fluorescent moiety covalently-conjugated to the spacer P should be at least 1.02 and up to 10.000.000 times fold higher compared to the k obtained for the same fluorescent moiety non-conjugated to the spacer P.

Fluorescent moiety X and antigen recognizing moiety Y can be bound covalently or quasi-covalently to spacer P. The terms "covalently or quasi-covalently" refers bonds between X and P and Y and P having a dissociation constant of $\leq 10^{-9}$ M.

The process of the invention may be performed in one or more sequences of the steps a) to e). After each sequence, the fluorescent moiety is degraded by irradiation with light.

The terms "quenching" and "bleaching" are used interchangeably herein, and should be understood to mean the diminution of fluorescence intensity from the labeled biological sample, as result of an alteration of the fluorophore by radiation. For example, "quenching" or "bleaching" of the fluorescent moiety X may be achieved by oxidation initiated by the radiation and/or by cleaving the fluorescent moiety X from spacer P and removing the unbound fluorescent moiety from the labelled target by washing.

Accordingly, the quenching system used in the method of the invention comprises at least one light source.

Accordingly, the quenching unit used in the present invention may be provided with more than one light sources emitting quenching radiation of different wavelengths. For example the quenching unit may be provided with 1-5 light sources which have a combined emission spectrum in the range of 350-850 nm, preferable 450-650 nm. The emission of the light sources may optically combined to irradiate the sample simultaneously or subsequently. For example, the quenching unit may be provided with three light sources emitting in the ranges 450-500 nm (blue), 520-560 nm (green) and 630-650 nm (red). In another embodiment only one light source is provided, emitting light in the range 350-850 nm, preferable 450-650 nm. The advantage of separate light sources is that the sample is exposed to radiation only necessary to quench (eliminate) the fluorescence dye thereby avoiding unnecessary exposure of the sample to radiation with other wavelengths. The radiation of the separate light sources may be combined by appropriate devices like mirrors or optical waveguide like optical fibre.

After and/or before each sequence, a washing step may be performed to remove unwanted material like unbound conjugates moieties and/or unbound fluorescent moieties X from the sample.

The quenching process as described may be further enhanced by adding oxidative agents. Oxidative agents may be for example $O_2$, $H_2O_2$, peroxides or DMSO. The oxidative agents added may generate the active oxidative species, which, calculated as $O_2$ should be present in concentrations of 0.1 to 5 ppm, preferable 2 to 5 ppm.

Target Moiety

The target moiety to be detected with the method of the invention can be on any biological specimen, like tissues slices, cell aggregates, suspension cells, or adherent cells. The cells may be living or dead. Preferable, target moieties are antigens expressed intracellular or extracellular on biological specimen like whole animals, organs, tissues slices, cell aggregates, or single cells of invertebrates, (e.g., *Caenorhabditis elegans, Drosophila melanogaster*), vertebrates (e.g., *Danio rerio, Xenopus laevis*) and mammalians (e.g., *Mus musculus, Homo sapiens*).

Spacer P

The spacer P comprises polyethyleneglycol according to general formula I, which can be based on ethylene glycol grafted on polyhydroxy compounds, polyamino compounds and polythio compounds. Such compounds or precursors thereof are commercially available from Nanocs Inc., Sigma-Aldrich or NOF Corporation Preferred precursors are polyhydroxy compounds, such as pentaerythritol with four hydroxyl group as attachment points for 3 to 4 polyether residues via ether bonds, dipentaerythritol with six hydroxyl groups as attachment points for 3 to 6 polyether branches via ether bonds, tripentaerythritol or hexaglycerol with eight hydroxyl groups as attachment points for 3 to 8 polyether branches via ether bonds.

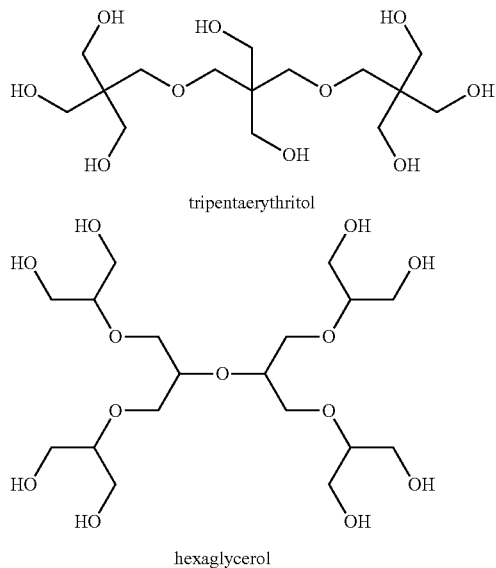

The polyhydroxy compounds may be substituted by ether monomer units which can be homopolymeric or copolymeric, i.e., alternating or block copolymers. Polyether residues can be linear or branched.

In order to achieve a covalent bond of the spacer P to Y and X, the polyethyleneglycol of formula I may be provided with at least two reactive groups known in the field of fluorescence conjugates, sich as acetal, acid anhydride, acid chloride, acyl azide, acyl halides, acyl nitriles, acyl phosphate, acylamides, aldehyde, alkoxyl, alkyl azide, alkyl sulfonate, alkyne, allyl, amide, anhydrides, aryl halides, azidonitrophenyl, aziridines, boronates, carbamates, carbodiimides, carbonate ester, carboxylates, carboxylic acids, diayzoalkanes, dichlorotriazine, diene, disulfide, enamine, epoxides, fluorobenzene, fluorophenyl ester, glyoxal, haloacetamides, haloplatinate, halotiazines, hemiacetal, hemiketal, highly strained cycloalkanes, highly strained cycloalkenes, highly strained cycloalkynes, hydrazides, hydrazine, hydroxyl, hydroxylamines, imidazole, imidoester, imine, iodoacetamide, isocyanate, isothiocyanate, ketal, ketones, lactones, maleimide, monochlorotriazine, N-hydroxysuccinimid ester, nitrile, nitro, oximes, pentafluorophenyl ester, peroxides groups, phosphoramidite, primary amines, secondary amines, silyl halides, sulfhydryl groups, sulfide, sulfodichlorophenyl ester, sulfonate esters, sulfone, sulfonyl halides, tertiary amines, tetrafluorophenyl ester, thioamide, thioester, thioether, thiolcarboxylic acids, active esters, alkene or conjugated alkene groups.
with Z=at least one fluorescent moiety X and at least one antigen recognizing moiety X; and p is an integer ranging from 1 to 500.

Fluorescent Moiety X

Suitable fluorescent moieties X are those known from the art of immunofluorescence technologies, e.g., flow cytometry or fluorescence microscopy. In these embodiments of the invention, the target moiety labelled with the conjugate is detected by exciting the fluorescent moiety X and detecting the resulting emission (photoluminescence). In this embodiment, the fluorescent moiety X is preferable a fluorescent moiety.

Useful fluorescent moieties X might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyrromethenes, pyridyloxazole or metallo-organic complexes, such as Ru, Eu, Pt complexes. Besides single molecule entities, clusters of fluorescent proteins or small organic molecule dyes, as well as nanoparticles, such as quantum dots, upconverting nanoparticles, gold nanoparticles, dyed polymer nanoparticles can also be used as fluorescent moieties.

In another embodiment of the invention the target labelled with the conjugate is not detected by radiation emission, but by absorption of UV, visible light, or NIR radiation. Suitable light-absorbing detection moieties are light absorbing dyes without fluorescence emission, such as small organic molecule quencher dyes like N-aryl rhodamines, azo dyes, and stilbenes.

In another embodiment, the light-absorbing fluorescent moieties X can be irradiated by pulsed laser light, generating an photoacoustic signal.

In a variant of the invention, the fluorophore X is substituted with one more water solubility imparting substituents selected from the group consisting of sulfonates, phosphonates, phosphates, polyethers, sulfonamides and carbonates. It is particularly advantageous to use fluorescent dyes with sulfonate substituents, such as dyes of the ALEXA FLUOR® family provided by Thermo Fisher Scientific Inc. The degree of sulfonate substitution per fluorophore may be 2 or more, i.e., for rhodamine dyes or cyanine dyes. The use of sulfonated dyes compared to unsulfonated dyes leads to even brighter conjugates of fluorophores multimerized on a polyether scaffold For example, T helper cells stained with a CD4 conjugate of Alexa Fluor 488 multimerized on a branched PEG (PEG-AF488) are almost twice as bright (mean MFI 98) as T helper cells stained with a CD4 conjugate of fluorescein multimerized on a branched PEG (PEG-FAM) (mean MFI 55).

Suitable commercial available fluorescent moieties may be selected from the product line "Vio" from Miltenyi Biotec GmbH, or FITC, or Promofluor, or Alexa Dyes and/or BIODYP® dyes from Thermofisher, or Cyanines from Lumiprobe.

Antigen Recognizing Moiety Y

The term "antigen recognizing moiety Y" refers to any kind of antibody, fragmented antibody or fragmented antibody derivatives, directed against the target moieties expressed on the biological specimens, like antigens expressed intracellular or extracellular on cells. The term relates to fully intact antibodies, fragmented antibody or fragmented antibody derivatives, e.g., Fab, Fab', F(ab')2, sdAb, scFv, di-scFv, nanobodies. Such fragmented antibody derivatives may be synthesized by recombinant procedures including covalent and non-covalent conjugates containing these kind of molecules. Further examples of antigen recognizing moieties are peptide/MHC-complexes targeting TCR molecules, cell adhesion receptor molecules, receptors for costimulatory molecules, artificial engineered binding molecules, e.g., peptides or aptamers which target, e.g., cell surface molecules.

The conjugate used in the method of the invention may comprise up to 100, preferable 1-20 antigen recognizing moieties Y. The interaction of the antigen recognizing moiety with the target antigen can be of high or low affinity. Binding interactions of a single low-affinity antigen recognizing moiety is too low to provide a stable bond with the antigen. Low-affinity antigen recognizing moieties can be multimerized by conjugation to the enzymatically degradable spacer P to furnish high avidity. When the spacer P is enzymatically cleaved, the low-affinity antigen recognizing moieties will be monomerized which results in a complete removal of the fluorescent moiety X, the spacer P and the antigen recognizing moiety Y.

Preferable, the term "Antigen recognizing moiety Y" refers to an antibody directed against antigen expressed by the biological specimens (target cells) intracellular, like IL2, FoxP3, CD154, or extracellular, like CD19, CD3, CD14, CD4, CD8, CD25, CD34, CD56, and CD133.

The antigen recognizing moieties Y, especially antibodies, can be coupled to the spacer P through side chain amino or sulfhydryl groups. In some cases the glycosidic side chain of the antibody can be oxidized by periodate resulting in aldehyde functional groups.

The antigen recognizing moiety Y can be covalently or non-covalently coupled to the spacer P. Methods for covalent or non-covalent conjugation are known by persons skilled in the art and the same as mentioned for conjugation of the fluorescent moiety X.

The method of the invention is especially useful for detection and/or isolation of specific cell types from complex mixtures and may comprise more than one sequential sequences of the steps a)-e). The method may use a variety of combinations of conjugates. For example, a conjugate may comprise antibodies specific for two different epitopes, like two different anti-CD34 antibodies. Different antigens may be addressed with different conjugates comprising different antibodies, for example, anti-CD4 and anti-CD8 for differentiation between two distinct T-cell-populations or anti-CD4 and anti-CD25 for determination of different cell subpopulations like regulatory T-cells.

Conjugates Xn-P-Ym

Preferable, conjugates used in the method of the invention are provided with spacer groups P having 100 to 1000 repeating units of ethylene glycol.

For example, conjugates used in the method of the invention are compounds according to the general formula II and III, each with Z=at least one fluorescent moiety X and at least one antigen recognizing moiety X; and p is an integer ranging from 2 to 500.

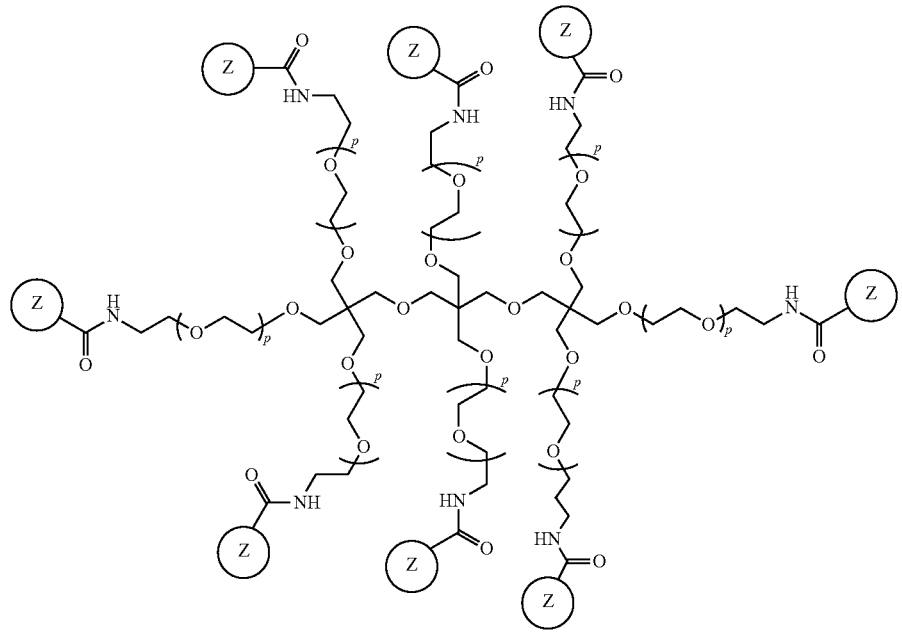

(II)

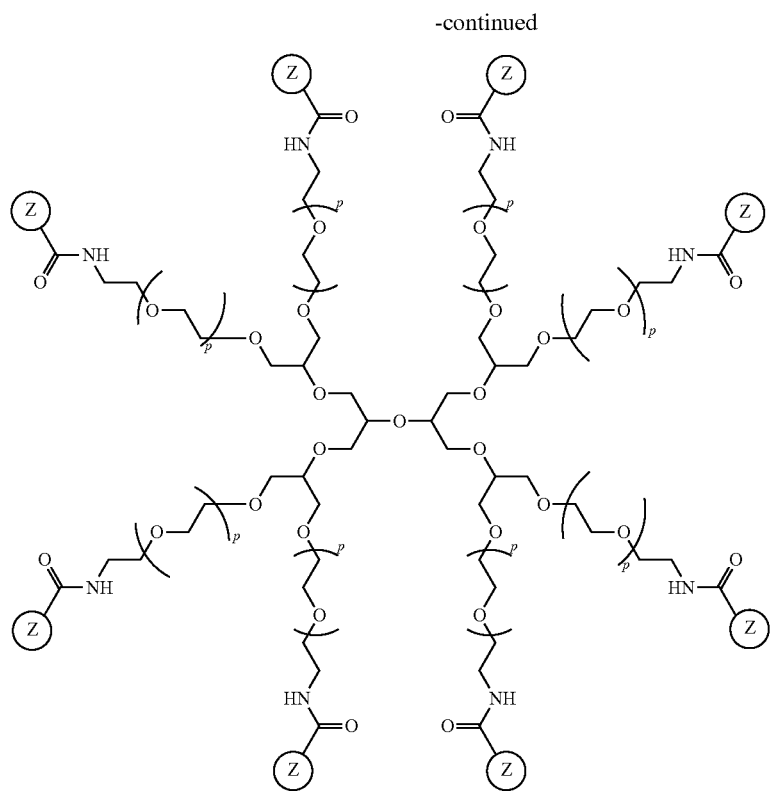

(III)

Cell Detection Methods

The method and equipment to detect the target labelled with the conjugate $X_n$—P—$Y_m$ is determined by the fluorescent moiety X.

Targets labelled with the conjugate are detected by exciting the fluorescent moiety X and analysing the resulting fluorescence signal. The wavelength of the excitation is usually selected according to the absorption maximum of the fluorescent moiety X and provided by LASER or LED sources as known in the art. If several different detection moieties X are used for multiple colour/parameter detection, care should be taken to select fluorescent moieties having not overlapping absorption spectra, at least not overlapping absorption maxima. In case of a fluorescent moieties as fluorescent moiety the targets may be detected, e.g., under a fluorescence microscope, in a flow cytometer, a spectrofluorometer, or a fluorescence scanner. Light emitted by chemiluminescence can be detected by similar instrumentation omitting the excitation.

Use of the Method

The method of the invention can be used for various applications in research, diagnostics and cell therapy, like in fluorescence microscopy, flow cytometer, spectrofluorometry, cell separation, pathology or histology.

In a first variant of the invention, biological specimens like cells are detected for counting purposes i.e. to establish the amount of cells from a sample having a certain set of antigens recognized by the antigen recognizing moieties of the conjugate.

In another variant, the biological specimens detected by the conjugate in step c) are separated from the sample by optical means, electrostatic forces, piezoelectric forces, mechanical separation or acoustic means. For this purpose, the biological specimens detected by the conjugate in step d) are separated from the sample according to their detection signal to one or more populations simultaneously or subsequent before performing step e) by optical means, electrostatic forces, piezoelectric forces, mechanical separation or acoustic means.

In another variant of the invention, the location of the target moieties like antigens on the biological specimens recognized by the antigen recognizing moieties of the conjugate is determined. Such techniques are known as "Multi Epitope Ligand Cartography", "Chip-based Cytometry" or "Multiomyx" and are described, for example, in EP 0810428, EP1181525, EP 1136822 or EP1224472. In this technology, cells are immobilized and contacted with antibodies coupled to fluorescent moiety. The antibodies are recognized by the respective antigens on the biological specimen (for example on a cell surface) and after removing the unbound marker and exciting the fluorescent moieties, the location of the antigen is detected by the fluorescence emission of the fluorescent moieties. In certain variants, instead of antibodies coupled to fluorescent moieties, antibodies coupled to moieties detectable for MALDI-Imaging or CyTOF can be used. The person skilled in the art is aware how to modify the technique based on fluorescent moiety to work with these detection moieties.

The location of the target moieties is achieved by a digital imaging device with a sufficient resolution and sensitivity in for the wavelength of the fluorescence radiation. The digital imaging device may be used with or without optical enlargement for example with a fluorescence microscope. The resulting images are stored on an appropriate storing device like a hard drive, for example in RAW, TIF, JPEG, or HDF5 format.

In order to detect different antigens, different antibody-conjugates having the same or different fluorescent moiety or antigen recognizing moiety Y can be provided. Since the parallel detection of fluorescence emission with different wavelengths is limited, the antibody-fluorochrome-conjugates are utilized sequentially individually or in small groups (2-10) after the other.

In yet another variant of the method according to the invention, the biological specimens—especially suspension cells—of the sample are immobilized by trapping in microcavities or by adherence.

In general, the method of the invention can be performed in several variants. For example, the conjugate not recognized by a target moiety can be removed by washing for example with buffer before the target moiety labelled with the conjugate is detected.

In a variant of the invention, at least two conjugates are provided simultaneously or in subsequent staining sequences, wherein each antigen recognizing moiety Y recognizes different antigens. In an alternative variant, at least two conjugates can be provided to the sample simultaneously or in subsequent staining sequences, wherein each conjugate comprises a different enzymatically degradable spacer P which is cleaved by different enzymes. In both cases, the labelled target moieties can be detected simultaneously or sequentially. Sequential detection may involve enzymatically degrading of at least one spacer molecule P or subsequent enzymatically degrading of the spacer molecule P with optionally intermediate removing (washing) of the non-bonded moieties.

EXAMPLES

In order to illustrate the general kinetics involved in photodegradation, FIG. 1 shows a schematic curve obtained for photodegradation of a xanthene dye by light fitted with a mono-exponential decay curve such as $f(x)=y_0 * e^{-k*x}$, where $tau=1/k$ and $t_{1/2}=tau*\ln(2)$ is the half-life.

To measure the kinetics of photodegradation, organic fluorophores (i.e. coumarines, xanthenes, rhodamines, cyanines, among others) were either dissolved in DMSO and diluted in PBS or directly dissolved in PBS such that the concentration was adjusted to obtain an absorbance at their respective maxima of ca. 0.3 A.U. with a path-length of 1 cm. This way all solutions are normalized by their absorbance and comparable. Then the solution was placed inside a 3 window fluorescence quartz cuvette with low head space and an air-tight top to avoid evaporation and sample concentration. The sample in the cuvette was then irradiated for fixed amount of times and both the absorbance and emission spectra were recorded. Intensity values are their maxima were used to plot vs irradiate time and then a mathematical fit to mono-exponential decays was performed by appropriate computer software to obtain a curve similar to the one shown in FIG. 1. Characteristic decay times (k) were used to calculate half-life among other parameters.

Figure 2:
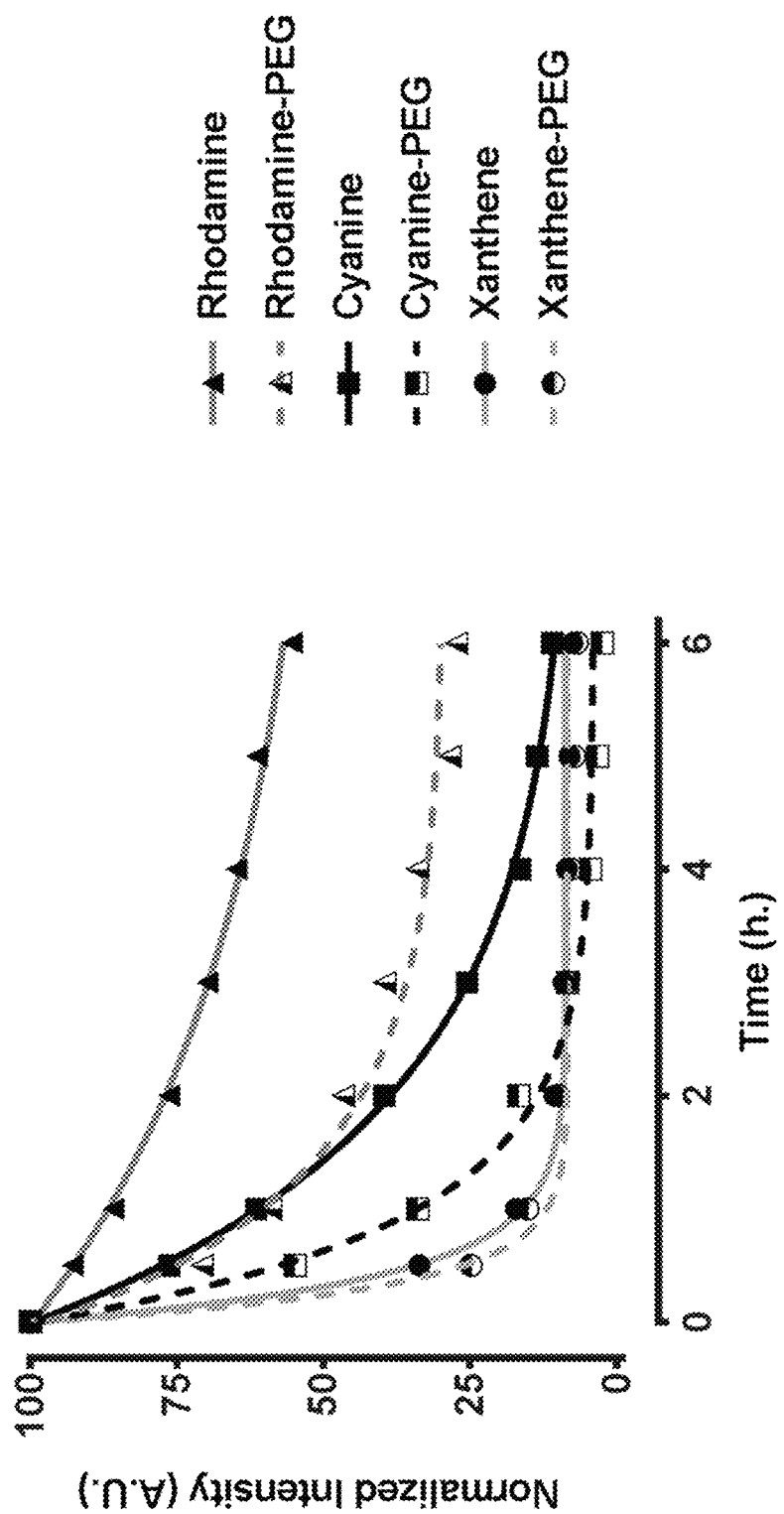
FIG. 2 shows photodegrading curves for a series of dyes belonging to different chemical classification according to the nature of their chromophore (i.e. coumarines, xanthenes, rhodamines, cyanines), showing all dye classes are sensitive to such light-induced degradation

FIG. 2. shows photodegrading decay curves for a series of dyes belonging to a different chemical classification according to the nature of their chromophore (i.e. xanthenes, rhodamines, cyanines), and their PEGylated version where each dye is covalently conjugated to branched PEG.

The data shown in FIG. 2 shows that: a) all dyes classes are sensitive to light photo-degradation and b) when conjugated to a branched PEG as defined in this application the rate of photodegradation is higher.

Example

Photodegradation curves were obtained for a Cyanine dye under four different conditions:

i) not bond to a spacer and free in solution (comparison)

ii) covalently attached to a linear PEG pf 20 kDa (comparison)

iii) free in solution containing 5% PEG 20 kDA not covalently attached (comparison)

iv) covalently attached to a branched PEG of 20 kDa (according to the invention)

Figure 3:
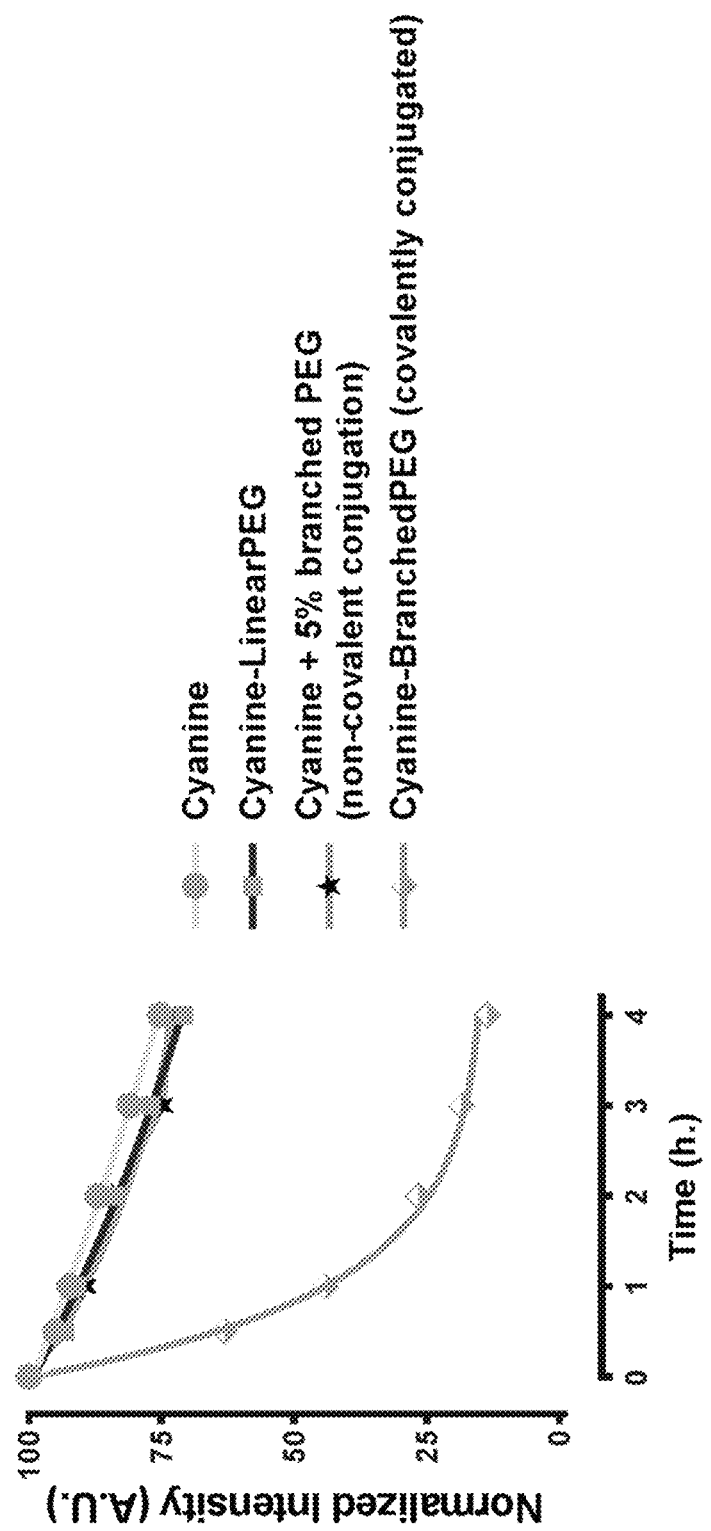
FIG. 3 shows photodegrading curves for a cyanine dye under four different conditions.

FIG. 3 illustrates that both covalently conjugated but linear PEGs and non-conjugated but branched PEG (5% PEG) of same molecular weight do not exert an effect on the degradation rate of a fluorophore.

Accordingly, only conjugates as disclosed in the present application i.e. branched PEGs covalently conjugated to a fluorescent moiety have the accelerated light-induced photodegradation as required by the method of the invention.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A method for detecting a target moiety in a sample of biological specimens comprising:

a) providing at least one conjugate with the general formula III:

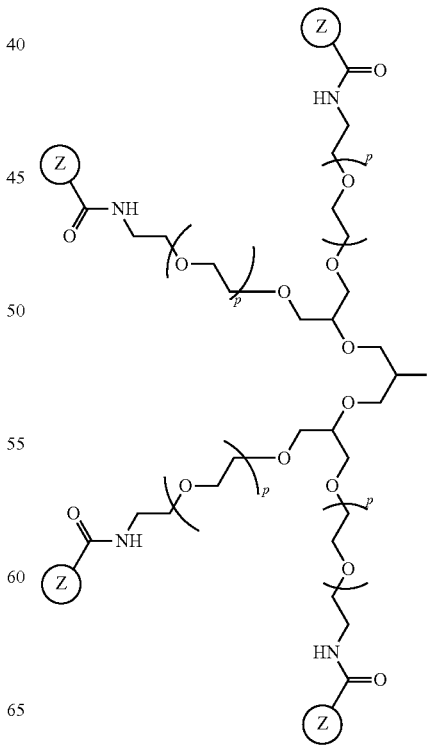

-continued

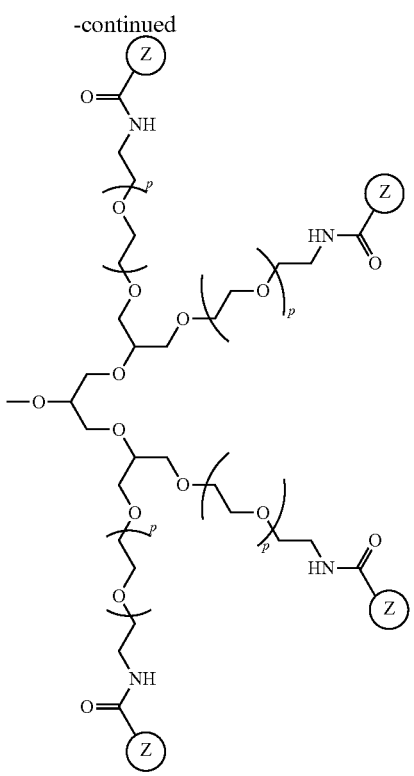

wherein Z is at least one fluorescent moiety X and at least one antigen recognizing moiety Y; and p is an integer ranging from 27 through 112;

b) contacting the sample of biological specimens with the at least one conjugate, thereby labelling the target moiety recognized by the at least one antigen recognizing moiety Y with the conjugate;

c) exciting the labelled target moieties with light having a wavelength within the absorbance spectrum of the at least one fluorescent moiety X;

d) detecting the labelled target moieties by detecting the fluorescence radiation emitted by the at least one fluorescent moiety X; and e) degrading the at least one fluorescent moiety X of the labelled target moieties by irradiating the conjugate with light having a wavelength within the absorbance spectrum of the at least one fluorescent moiety X for a time sufficient to deliver enough energy to reduce the fluorescence radiation emitted by the at least one fluorescent moiety X at least by 75% of the initial fluorescence radiation.

2. The method according to claim 1, wherein the at least one fluorescent moiety X is selected from the group consisting of xanthene dyes, rhodamine dyes, coumarine dyes, cyanine dyes, pyrene dyes, oxazine dyes, pyridyl oxazole dyes and pyrromethene dyes.

3. The method according to claim 1, wherein the at least one fluorescent moiety X is substituted with one more water solubility imparting substituents selected from the group consisting of sulfonates, phosphonates, phosphates, sulfonamides, polyethers and carbonates.

4. The method according to claim 1, wherein the at least one antigen recognizing moiety Y is at least one biomolecule selected from group consisting of an immunoglobulin, antibody, fragmented antibody, Fab, Fab', F(ab')$_2$, sdAb, scFv, and di-scFv, each of naturally or recombinant origin.

5. The method according to claim 1, wherein the at least one antigen recognizing moiety Y is at least one biomolecule selected from the group consisting of peptide/MHC-complexes, receptors for cell adhesion or costimulatory molecules, receptor ligands, antigens, hapten binders, avidin, streptavidin, neutravidin, aptamers, primers and ligase substrates.

6. The method according to claim 1, wherein the at least one antigen recognizing moiety Y is an antibody, an fragmented antibody, an fragmented antibody derivative, peptide/MHC-complexes targeting TCR molecules, cell adhesion receptor molecules, receptors for costimulatory molecules or artificial engineered binding molecules.

* * * * *